United States Patent
Lowery et al.

(10) Patent No.: US 10,278,961 B2
(45) Date of Patent: May 7, 2019

(54) ADMINISTRATION OF BERBERINE METABOLITES

(71) Applicant: Keto Patent Group, Inc., Melissa, TX (US)

(72) Inventors: Ryan Lowery, Tampa, FL (US); Jacob Wilson, Tampa, FL (US); Shawn Wells, Lewisville, TX (US); Terry LaCore, Melissa, TX (US)

(73) Assignee: Keto Patent Group, Inc., Melissa, TX (US)

( * ) Notice: Subject to any disclaimer, the term of this patent is extended or adjusted under 35 U.S.C. 154(b) by 0 days.

(21) Appl. No.: 15/491,933

(22) Filed: Apr. 19, 2017

(65) Prior Publication Data
US 2017/0296520 A1    Oct. 19, 2017

Related U.S. Application Data

(60) Provisional application No. 62/324,794, filed on Apr. 19, 2016.

(51) Int. Cl.
| | |
|---|---|
| *A61K 31/4355* | (2006.01) |
| *A61K 9/00* | (2006.01) |
| *A61K 38/00* | (2006.01) |
| *A61K 47/54* | (2017.01) |
| *A61K 9/107* | (2006.01) |

(52) U.S. Cl.
CPC ........ *A61K 31/4355* (2013.01); *A61K 9/0095* (2013.01); *A61K 38/005* (2013.01); *A61K 47/544* (2017.08); *A61K 9/1075* (2013.01)

(58) Field of Classification Search
CPC ................. C07D 455/03; A61K 314/4355
See application file for complete search history.

(56) References Cited

U.S. PATENT DOCUMENTS

| | | | |
|---|---|---|---|
| 2010/0113494 A1* | 5/2010 | Hu | C07D 455/03 514/280 |
| 2014/0350105 A1 | 11/2014 | D'Agostino et al. | |
| 2015/0063140 A1 | 3/2015 | Yi et al. | |

OTHER PUBLICATIONS

International Search Report and Written Opinion for PCT/US17/28466 dated Jul. 5, 2017 (9 pages).

* cited by examiner

*Primary Examiner* — Paul V Ward

(74) *Attorney, Agent, or Firm* — Ferguson Braswell Fraser Kubasta PC; Elizabeth Philip Dahm; Kelly J. Kubasta

(57) ABSTRACT

In various implementations, berberine metabolites, such as dihydroberberine and/or tetrahydroberberine, may be administered to manage blood glucose levels, increase ketone levels (e.g., blood concentration of ketones), and/or for therapeutic purposes in humans. The administration of a pharmaceutically effective amount of berberine metabolites, such as dihydroberberine, may reduce fasting blood glucose levels, improve glucose tolerance, and/or improve blood ketone response. In some implementations, berberine metabolites may be administered with one or more other compounds.

20 Claims, 4 Drawing Sheets

| Subject 1 | | Subject 2 | | Subject 3 | | Subject 4 | | Subject 5 | |
|---|---|---|---|---|---|---|---|---|---|
| 1 | 500 mg DHBB | 1 | 250 mg DHBB | 1 | 250 mg DHBB | 1 | 500 mg DHBB | 1 | 500 mg DHBB |
| 2 | 250 mg DHBB | 2 | 500 mg DHBB | 2 | 500 mg DHBB | 2 | 250 mg DHBB | 2 | 500 mg BB HCL |
| 3 | 500 mg BB HCL | 3 | 500 mg BB HCL | 3 | 500 mg BB HCL | 3 | 500 mg BB HCL | 3 | 250 mg DHBB |

| Subject | Condition | Baseline | 30 minutes | 60 minutes | 90 minutes | 120 minutes | 180 minutes |
|---|---|---|---|---|---|---|---|
| 1 | 500 mg Berb HCL | 83 | 142 | 121 | 108 | 93 | 88 |
| 2 | 500 mg Berb HCL | 90 | 113 | 88 | 112 | 131 | 83 |
| 3 | 500 mg Berb HCL | 103 | 103 | 149 | 96 | 83 | 80 |
| 4 | 500 mg Berb HCL | 96 | 96 | 97 | 101 | 102 | 87 |
| 5 | 500 mg Berb HCL | 88 | 88 | 133 | 104 | 81 | 80 |
| Average | | 92 | 92 | 117.6 | 104.2 | 98 | 83.6 |
| 1 | 500 mh Dihydro | 76 | 97 | 117 | 98 | 97 | 96 |
| 2 | 500 mh Dihydro | 74 | 109 | 106 | 101 | 96 | 92 |
| 3 | 500 mh Dihydro | 93 | 131 | 102 | 102 | 102 | 113 |
| 4 | 500 mh Dihydro | 81 | 102 | 119 | 94 | 90 | 84 |
| Average | | 81 | 110 | 111 | 98.75 | 96.25 | 96.25 |
| 1 | 250 mh Dihydro | 88 | 139 | 116 | 114 | 100 | 94 |
| 2 | 250 mh Dihydro | 92 | 93 | 102 | 114 | 96 | 88 |
| 3 | 250 mh Dihydro | 108 | 133 | 104 | 103 | 101 | 103 |
| 4 | 250 mh Dihydro | 77 | 116 | 105 | 100 | 104 | 97 |
| 5 | 250 mh Dihydro | 91 | 130 | 92 | 95 | 88 | 88 |
| Average | | 91.2 | 122.2 | 103.8 | 105.2 | 97.8 | 94 |

ADMINISTRATION OF BERBERINE METABOLITES

CROSS-REFERENCE TO RELATED APPLICATIONS

This application claims the benefit of U.S. Provisional Patent Application No. 62/324,794, entitled "ADMINISTRATION OF DIHYDROBERBERINE", filed on Apr. 19, 2016, which is incorporated by reference for all purposes.

TECHNICAL FIELD

The present invention relates to managing metabolic and therapeutic functions by administering berberine metabolites.

BACKGROUND

Berberine is a naturally occurring substance commonly found in Goldenseal (*Hydrastis canadensis*), Oregon grape (*Berberis aquifolium*), Barberry (*Berberis vulgaris*), Chinese Goldthread (*Coptis chinensis, Phellodendron chinense*, and *Phellodendron amurense*. Berberine has been administered to humans and found to have an effect on inflammation and as well as having some antimicrobial properties. Berberine has also shown potential for lowering fasting blood glucose; however adverse gastrointestinal effects appeared to accompany the administration in amounts to effectively lower fasting blood glucose (Yin et al. "Efficacy of Berberine in Patients with Type 2 Diabetes," Metabolism. 2008 May; 57(5): 712-717). The bioavailability of traditional berberine has been shown in some studies to be below 70% in animal models which could affect how much is being absorbed and actually utilized in the body (Chen, W., Miao, Y. Q., Fan, D. J., Yang, S. S., Lin, X., Meng, L. K., & Tang, X. (2011). Bioavailability study of berberine and the enhancing effects of TPGS on intestinal absorption in rats. Aaps Pharmscitech, 12(2), 705-711.)

SUMMARY

In various implementations, one or more berberine metabolites (e.g., dihydroberberine and/or tetrahydroberberine) may be administered to manage glucose tolerance and/or increase ketones (e.g., blood concentration and/or urine concentration of ketones) in humans. For example, a pharmaceutically effective amount of berberine metabolites (e.g., dihydroberberine and/or tetrahydroberberine) may be administered to healthy and/or nonhealthy adults. For example a pharmaceutically effective amount of berberine metabolites may be administered to a human with diabetes or other metabolic disorder impacting glucose tolerance. The berberine metabolites may regulate glucose and/or lipid metabolism. In some implementations, administration of a pharmaceutically effective amount of berberine metabolites may be therapeutic to humans with diabetes, glucose intolerance, metabolic syndrome, dyslipidemia, and/or obesity/overweight. In some implementations, administration of berberine metabolites may have ergogenic (e.g., performance enhancing) and/or body composition benefits for some individuals (e.g., generally healthy; athletic; etc.) via glucose disposal, insulin sensitivity and ketone sensitivity. In some implementations, administration of berberine metabolite(s) may lower glycation (e.g., measured by HA1c levels) which may provide anti-aging properties.

In various implementations, the berberine metabolite composition administered to an individual may include dihydroberberine and/or tetrahydroberberine. For example, the composition may be orally administered in any appropriate delivery vehicle, such as via tablets, capsules, food products, and/or beverage products.

In some implementations, one or more berberine metabolites may be administered with one or more additional compounds. The additional compounds, such as ketone sensitizers, may be capable of independently inducing ketosis. The additional compounds may be utilized to maintain and/or promote ketosis in humans. For example, the additional compounds may include one beta-hydroxybutyrate compound; butyrate; short chain, medium chain, and/or long chain fatty acids or esters thereof; and/or combinations there of which may be administered with a berberine metabolite, such as dihydroberberine.

In various implementations, a pharmaceutically effective amount of dihydroberberine may be administered to an individual to managing glucose tolerance (e.g., decrease and/or maintain blood glucose level, decrease and/or maintain fasting blood glucose, increase ability to process glucose, etc.).

Implementations may include one or more of the following features. The administration of dihydroberberine may reduce fasting glucose levels. The dihydroberberine may be administered as a complexed composition. The complexed composition may include phytosomes and/or liposomes. The dihydroberberine may be a microemulsion including dihydroberberine. The pharmaceutically effective amount of dihydroberberine may include approximately 25 mg to approximately 800 mg of dihydroberberine, in some implementations. The dihydroberberine may be orally administered as a capsule, tablet, a food product, and/or beverage product. The dihydroberberine may be administered at least once daily (e.g., for a period of time, when desired by the user, etc.). In some implementations, a Cytochrome P450 inhibitor may be administered approximately concurrently. Administration of the Cyctochrome P450 inhibitor may allow decreasing of the amount of dihydroberberine administered to be sufficient to achieve the desired results (e.g., the same level of glucose management as a predetermined amount of dihydroberberine, a normal range of fasting glucose levels per health guidelines, normal level of blood glucose level per health guidelines, etc.).

In various implementations, administering, to an individual, a pharmaceutically effective amount of dihydroberberine may increase blood ketone levels.

Implementations may include one or more of the following features. The dihydroberberine may be administered approximately concurrently with meals. In some implementations, a pharmaceutically effective amount of an additional compound may be administered with the dihydroberberine, where the additional compound is capable of inducing ketosis independently (e.g., ketone sensitizer). The dihydroberberine and additional compound may be administered approximately concurrently. The dihydroberberine and additional compound may be administered at least one time daily (e.g., for a period of time, per user desire, per doctor recommendation, until glucose level and/or blood ketone level is within a predetermined range, etc.).

In various implementations, composition may be capable of maintaining ketosis in an individual (e.g., within a predetermined time period of administration to the individual). The composition may include a pharmaceutically effective amount of dihydroberberine and an additional compound (e.g., a compound that can impact blood ketone levels independently, such as a ketone sensitizer). The amount of dihydroberberine administered to be pharmaceutically effective may be less than the amount of dihydroberberine administered to be pharmaceutically effective when the dihydroberberine is administered without the additional compound(s) (e.g., to achieve a predetermined level of ketosis and/or a range of blood ketone levels).

Implementations may include one or more of the following features. The additional compound(s) may include beta-hydroxybutyrate (e.g., R-beta-hydroxybutyrate and/or D,L-beta-hydroxybutyrate), butyrate, fatty acid, and/or ester of fatty acid. The additional compound may include R-beta-hydroxybutyrate (e.g., salt, polymer, and/or complexed with another compound such as an amino acid). The additional compound may include a beta-hydroxybutyrate salt, beta-hydroxybutyrate polymer, beta-hydroxybutyrate amino acid (e.g., R-beta-hydroxybutyrate amino acid mixture and/or complex, such as R-beta-hydroxybutyrate and leucine), and/or beta-hydroxybutyrate free acid(s). The dihydroberberine and additional compound may be administered approximately concurrently. The dihydroberberine and additional compound may be a mixture and/or a complexed compound. The additional compound may include a beta-hydroxybutyrate and at least one of a fatty acid or ester of a fatty acid, in some implementations.

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which:

FIG. 2 illustrates a table of subject responsiveness to an example administration protocol.

FIG. 4 a table with blood ketone levels for subjects after administration of an example administration protocol.

Like reference symbols in the various drawings indicate like elements.

DETAILED DESCRIPTION

Figure 1:
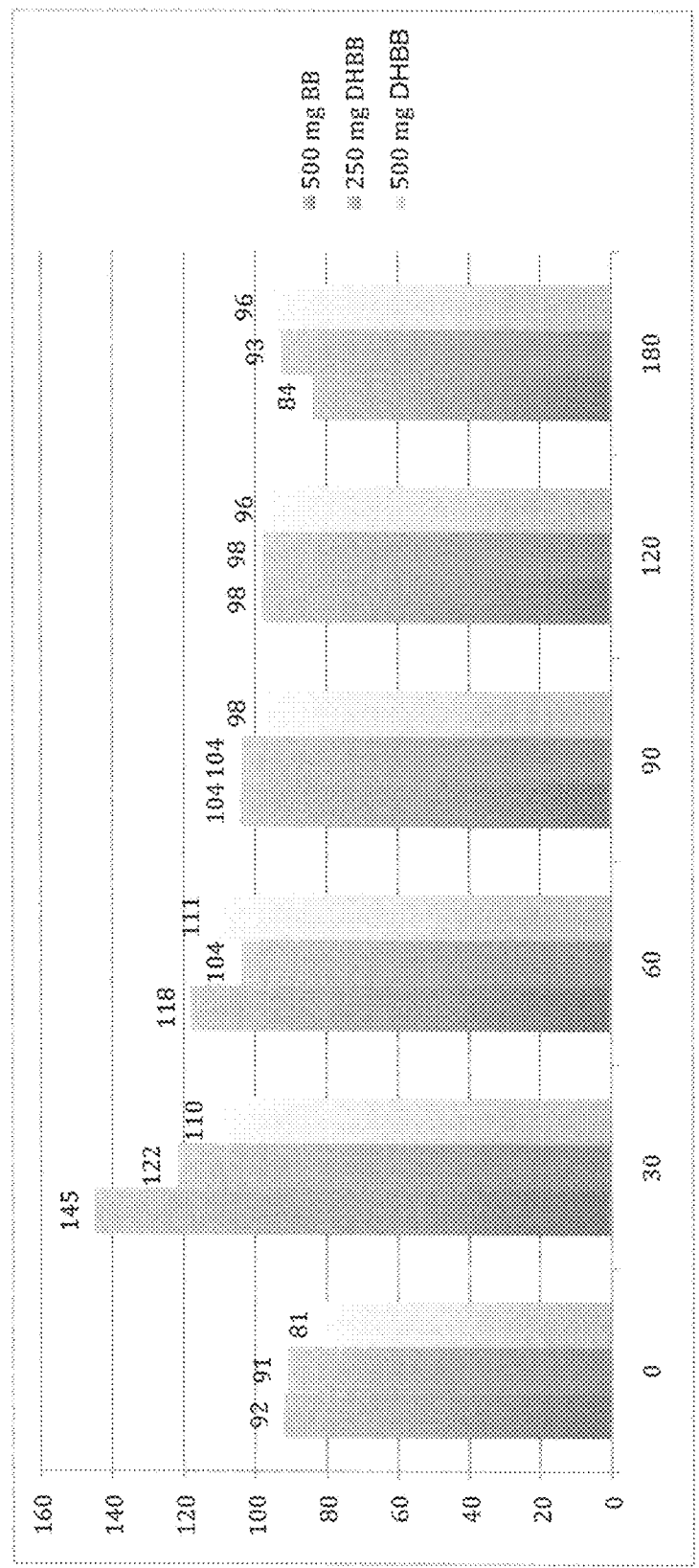
FIG. 1 illustrates table with glucose levels for subjects after administration of an example administration protocol.

In various implementations, administration of a pharmaceutically effective amount of berberine metabolites (e.g., dihydroberberine and/or tetrahydroberberine), derivates thereof and/or salts thereof may be administered to humans to manage blood glucose levels (e.g., reduce fasting blood glucose, improve glucose tolerance, etc.). In some implementations, administration of pharmaceutically effective amount of berberine metabolite(s) may maintain and/or increase ketone levels (e.g., blood and/or urine ketone concentration). In some implementations, administration of a pharmaceutically effective amount of berberine metabolite(s) (e.g., dihydroberberine and/or tetrahydroberberine) may be therapeutic to humans with diabetes, glucose intolerance, metabolic syndrome, dyslipidemia, and/or obesity/overweight. In some implementations, administration of berberine metabolites may have ergogenic (e.g., performance enhancing) and/or body composition benefits for some individuals (e.g., generally healthy; athletic; etc.) via glucose disposal, insulin sensitivity and ketone sensitivity. In some implementations, administration of a pharmaceutically effective amount of berberine metabolite(s) may lower glycation (e.g., measured by HA1c levels) which may provide anti-aging properties. The amount of berberine metabolite (e.g., dihydroberberine) administered to achieve a predetermined effect (e.g., fasting blood glucose level) may be less than the amount of berberine that would be required to achieve the same predetermined effect. In some implementations, one or more other compounds may be administered with the pharmaceutically effective amount of berberine metabolite, such as a ketone sensitizer (e.g., a compound that is capable of reducing and/or maintaining blood ketone levels independently, such as beta-hydroxybutyrate, short chain fatty acids, medium chain fatty acids, and/or long chain fatty acids).

In some implementations, a berberine metabolite composition may include dihydroberberine and/or tetrahydroberberine. Dihydroberberine ($C_{20}H_{19}NO_4$) is a compound that although related to berberine has properties that make it especially suited for managing glucose and/or increasing ketone levels (e.g., blood ketone levels). Dihydroberberine is a compound that is commercially available from sources such as, AdooQ Bioscience (Irving, Calif.).

Dihydroberberine may be more biologically available to humans than berberine. A first weight amount of dihydroberberine is capable of decreasing blood glucose levels greater than the same weight amount of berberine. A first weight amount of dihydroberberine may increase blood ketone levels more than the same weight amount of berberine. These are unexpected results since the inclusion of other function groups (hydro-) decreases the amount of "berberine" in the same weight amount of berberine. By increasing blood ketone levels, achieving a level of ketosis (e.g., blood ketone levels of 0.2 to 20 mM), maintaining a level of ketosis may be more easily obtainable during administration of dihydroberberine. Achieving ketosis may improve metabolic disorders, improve health (e.g., strength, mental acuity, etc.), increase weight loss, and/or increase fat loss (e.g., as opposed to lean muscle mass loss). Diabetes, various types of cancer, Alzheimer's, Parkinson's, Traumatic Brain Injury (TBI) PCOS, Metabolic Syndrome/Syndrome X, Obesity, Dyslipidemia, Aging, other metabolic disorders and/or other ketosensitive diseases and/or disorders may thus be affected by administration of dihydroberberine or tetrahydroberberine (e.g., since ketosis may be more easily achieved by individuals in which dihydroberberine has been administered).

In various implementations, the berberine metabolite may include tetrahydroberberine ($C_{20}H_{21}O_4N$). Tetrahydroberberine is a compound that although related to berberine has properties that make it especially suited for managing glucose and/or increasing ketone levels (e.g., blood ketone concentration). In some implementations, dihydroberberine and/or tetrahydroberberine may be complexed with other compounds such as phytosomes and/or liposomes. The berberine metabolite may be administered to a user via the complexed compound.

In various implementations, a pharmaceutically effective amount of berberine metabolite may be administered to humans to improve glucose tolerance. For example, an amount of approximately 25 mg to approximately 800 mg of dihydroberberine may be administered to a human. In some implementations, an amount of approximately 250 mg to approximately 300 mg may be administered to a human. The amount of dihydroberberine may be less than the amount of berberine required to achieve the same amount of glucose tolerance (e.g., a predetermined fasting glucose level, a predetermined range of blood glucose, a normal or other blood glucose level as determined by health guidelines, a normal or other fasting blood glucose as determined by health guidelines, etc.). In some implementations, an amount of dihydroberberine may provide the same level of glucose tolerance as at least double the same amount of berberine (e.g., the dihydroberberine may be at least twice as effective as berberine and thus half or less than half of a first amount of dihydroberberine would be required to achieve the same results as the first amount of berberine). This result is unexpected since one would expect berberine and dihydroberberine to have similar properties. Even with the known increase bioavailability of dihydroberberine over berberine, the ability to administer as little as half as much dihydroberberine as berberine to achieve similar results in glucose tolerance is unexpected. The ability to reduce the quantity of dihydroberberine administered to a human may reduce the side effects associated with administration, ease palatability (e.g., since taste may improve or be more easily masked with smaller dosages), ease administration (e.g., smaller dose size), reduce costs, etc. For example, since the same amount (e.g., molecular amount) of the "berberine" group is in berberine and dihydroberberine, decreasing the amount administered would decrease side effects associated with administration of berberine and/or related complexes.

In various implementations, one or more additional compounds may be administered with the berberine metabolite. The additional compounds may increase a benefit of the berberine metabolite (e.g., glucose management, decrease ketone levels, etc.) and/or provide additional benefits (e.g., increase mental acuity, increase fat loss, increase lean mass maintenance, increase strength, etc.) For example, an additional compound that is capable of impacting blood ketone levels (e.g., increasing and/or maintaining blood ketone levels, inducing ketosis, etc.), such as a ketone sensitizer, may be selected that increases ketosis (e.g., increase levels of ketones bodies in the blood).

In some implementations, the additional compounds (e.g., ketone sensitizers) may include a beta-hydroxybutyrate compound may be administered with the berberine metabolite (e.g., in a capsule such as a softgel; tablet; powdered supplement; ready-to-drink formulation; topical product; cosmeceutical product; foods such bars, cookies, gum, candy, functional foods; toothpaste, sublingual product; injection; intravenous fluids; beverages such as shots or energy shots; inhalers and/or other appropriate administration methods). A beta-hydroxybutyrate compound may include beta-hydroxybutyrate salts, beta-hydroxybutyrate monomer, beta-hydroxybutyrate polymers, and/or combinations thereof. For example, beta-hydroxybutyrate salts may include sodium beta-hydroxybutyrate, magnesium beta-hydroxybutyrate, calcium beta-hydroxybutyrate, lithium beta-hydroxybutyrate, potassium beta-hydroxybutyrate and/or combinations thereof. In some implementations, beta-hydroxybutyrate polymers may be selected for administration with dihydroberberine to administer beta-hydroxybutyrate (e.g., since beta-hydroxybutyrate polymers are metabolized in the body to administer beta-hydroxybutyrate). In some implementations, the beta-hydroxybutyrate administered may include organic salts, such as but not limited to, arginine beta-hydroxybutyrate, lysine beta-hydroxybutyrate, histidine beta-hydroxybutyrate, ornithine beta-hydroxybutyrate, creatine beta-hydroxybutyrate, agmatine beta-hydroxybutyrate, citrulline beta-hydroxybutyrate, and/or combinations thereof. The beta-hydroxybutyrate included in the composition may include R-beta-hydroxybutyrate (e.g., salts, polymers, complexes, etc.). The beta-hydroxybutyrate may include single isomer R-beta-hydroxybutyrate and/or polymer R-beta-hydroxybutyrate. In some implementations, beta-hydroxybutyrate may be administered with 1,3-butanediol, ethyl acetoacetate, ethyl beta-hydroxybutyrate.

In some implementations, the additional compound (e.g., that is capable of increasing blood ketone levels independently) may include a fatty acid and/or ester thereof. For example, the additional compound may include short chain, medium chain, and/or long chain fatty acids and/or esters thereof. The fatty acid(s) and/or esters thereof may include natural and/or synthesized compounds. For example, the additional compound may include coconut oil, butter, etc.

In some implementations, the composition may include more than one additional compound that is capable of increasing blood ketone levels and/or inducing ketosis independently (e.g., without dihydroberberine). For example, a medium chain fatty acid may be administered with the berberine metabolite and/or beta-hydroxybutyrate compound. In some implementations, an amino acid may be administered with dihydroberberine and R-beta-hydroxybutyrate (e.g., salt, polymer, and/or complex).

In various implementations, a composition may be administered as described that includes berberine metabolites (e.g., Dihydroberberine, tetrahydroberberine, etc.) and/or an additional compound that increases ketone levels (e.g., blood and/or urine), such as a ketone sensitizer. The additional compound(s) may include one or more beta-hydroxybutyrate compounds, short chain triglycerides, medium chain triglycerides, long chain triglycerides, combinations thereof and/or derivatives thereof. For example, one or more of the beta-hydroxybutyrate compounds and/or other ketone sensitizers (e.g., short chain triglycerides, medium chain triglycerides, long chain triglycerides) in U.S. patent application Ser. No. 15/491,924, to Lowery et al. and entitled "Administration of Beta-hydroxybutyrate and Related Compounds in Humans", filed Apr. 19, 2017 and U.S. Provisional Patent Application No. 62/324,798, to Lowery et al. and entitled "Administration of Beta-hydroxybutyrate and Related Compounds in Humans", filed Apr. 19, 2016, which is incorporated by reference to the extent that the teachings do not conflict with the present disclosure, may be utilized as a ketone sensitizer.

To achieve a predetermined amount of ketosis in an individual, an amount of an additional compound (e.g., capable of increasing ketone levels and/or inducing ketosis independently) administered with berberine metabolite(s) (e.g., Dihydroberberine, tetrahydroberberine, etc.) may be less than an amount of the additional compound administered without dihydroberberine. In some implementations, when berberine metabolite(s) (e.g., Dihydroberberine, tetrahydroberberine, etc.) is administered, as blood glucose levels decrease, unexpectedly, blood ketone levels may rise. Thus, less of the additional compound may be administered to achieve a predetermined blood ketone level (e.g., to maintain and/or promote a state of ketosis). For example, an additional compound, such as 10 grams of sodium beta-hydroxybutyrate may be administered to a 200 pound human to achieve a first level of ketosis (e.g., blood ketone level of 0.5 mM). When dihydroberberine is administered, the amount of the additional compound may be decreased. For example, when 250 mg of dihydroberberine is administered to a 200 pound human, 3 milligrams of sodium beta-hydroxybutyrate may be administered to achieve the first level of ketosis rather than 10 grams of sodium beta-hydroxybutyrate. Administration of the additional compound (e.g., that is capable of independently increasing ketone levels and/or inducing ketosis) may cause increase user satisfaction (e.g., less side effects from increased amounts of the additional compound and/or cation when salts of the additional compounds are included) and/or decreases costs (e.g., since less of the additional compound may be utilized), and enhance endogenous production (e.g. since blood glucose is lower, endogenous ketones may be elevated alongside the exogenous ketones)

In some implementations, the berberine metabolite(s) (e.g., dihydroberberine tetrahydroberberine, etc.) and the additional compound (e.g., capable of increasing ketone levels in the blood) may be administered approximately concurrently. For example, the dihydroberberine and ketone sensitizer may be provided in a capsule, pill, granular form (e.g., packet of granules), powdered form, liquid, gel, sublingual, transdermal and/or any other appropriate administration form.

In some implementations, one or more additives may be included in the composition, such as flavorings (e.g., natural and/or artificial), vitamins, minerals, binders, and/or any other appropriate additive. The additives may alter flavor, color, and/or texture. The additives may increase palatability and/or facilitate inclusion in a delivery vehicle (e.g., tablet, food product, beverage product such as a drink mix, etc.).

In some implementations, the berberine metabolite(s) may be processed to increase bioavailability, solubility, palatability, and/or combination with other compounds. For example, berberine metabolite(s) may be processed to form a microemulsion with other compounds (e.g., ketone sensitizer, liposome, phytosome, flavorings, etc.). In some implementations, the berberine metabolite may be microencapsulated (e.g., with and/or without other compounds such as ketone sensitizer, liposome, phytosome). Microemulsions may improve bioavailability and solubility as well as other agglomeration technologies. The microencapsulated berberine metabolite(s) (e.g., with or without combination with other compounds) may be a free flowing granular powder; dispersible in water; stable in acidic water solution for 30 minutes; allow controlled release in stomach and/or small intestines; inhibit glucose response (e.g., to any added materials); and/or allow delivery of a high butyrate content (e.g., around 70%), in some implementations. In some implementations, the berberine metabolite may be complexed with another compound (e.g., liposome, phytosome, and/or combinations thereof) and the berberine metabolite complex may be administered to the user to administer the berberine metabolite. Bioavailability enhancement via the mechanism of action for Cytochrome P450 inhibitors like naringen, bergamotin, piperine and its metabolites, as well as other bioavailability enhancers may be co-administered to enhance efficacy at lower therapeutic doses. Lowering the therapeutic dosage may decrease side effects and/or costs.

In various implementations, the berberine metabolite(s) (e.g., Dihydroberberine, tetrahydroberberine, etc.) and/or other compounds administered with the dihydroberberine may be administered on an appropriate administration schedule. For example, the Dihydroberberine/tetrahydroberberine and/or other compounds may be administered concurrently with meals, a predetermined amount of time before meals, a predetermined amount of time after meals, at regular or irregular time intervals, and/or according to other appropriate administration schedules. The berberine metabolite composition (e.g., including the berberine metabolite) may be administered on a periodic basis and/or as desired by a user. For example, the berberine metabolite composition may be administered to achieve a predetermined blood glucose level and/or fasting level. The administration of the composition (e.g., in the same and/or lower dosage) may be continued and/or discontinued once the predetermined level is achieved. The berberine metabolite composition may be administered as desired by a user in some implementations (e.g., to facilitate achieving user goals such as in strength training, for performance, for insurance testing, etc.). In some implementations, the amount of Dihydroberberine/tetrahydroberberine and/or other compounds administered at each dose may be the same and/or different.

In some implementations, the composition administered to an individual (e.g., human and/or any other appropriate animal) may include approximately 5 mg to approximately 1 gram of dihydroberberine. The composition may include one or more other compounds that may or may not be capable of increasing blood ketone levels independently, in some implementations. The composition may be administered (e.g., orally) approximately 1 to approximately 3 times daily. In some implementations, the composition may be provided in a delivery form such powder (e.g., that capable consumed separately, mixed with drinks, and/or food) and/or tablet. The administration of the composition may maintain ketosis levels for approximately 30 min to approximately 3 hours. The administration of the composition may maintain ketosis for longer than 3 hours. The administration of the composition may maintain blood glucose levels within a healthy range (e.g., as determined by a doctor, health guidelines, insurance guidelines, etc.). The administration of the composition may decreases blood glucose levels during a glucose challenge testing by over 25%, in some implementations. The administration of the composition may be capable of maintaining approximately 2 to approximately 3 times greater elevated ketones during carbohydrate intake (e.g., when compared with berberine and/or when compared with individuals not being administered dihydroberberine). The administration of the composition may increased fat metabolism by 10% (e.g., when compared with the individuals capability without administration of dihydroberberine).

In some implementations, the compound may include dihydroberberine and a beta-hydroxybutyrate. The composition may include one or more other compounds that may or may not be capable of increasing blood ketone levels independently, in some implementations. The composition may include approximately 5 mg to approximately 1 g of dihydroberberine and approximately 2 g of beta-hydroxybutyrate to approximately 10 g of beta-hydroxybutyrate. In some implementations, the composition may include approximately 400 mg to approximately 600 mg of dihydroberberine (e.g., approximately 500 mg) and approximately 4 to approximately 7 g of beta-hydroxybutyrate (e.g., 5 g of beta-hydroxybutyrate, such as R-beta-hydroxybutyrate). The composition may be administered (e.g., orally) approximately 1 to approximately 3 times daily. In some implementations, the composition may be provided in a delivery form such powder (e.g., that capable consumed separately, mixed with drinks, and/or food) and/or tablet. The combination of dihydroberberine and additional compounds that are capable of increasing ketones independently, such as beta-hydroxybutyrate, may increase ketones at a greater level than the expected additive amount. For example, a composition of 500 mg of dihydroberberine and 5 grams of beta-hydroxybutyrate and 5 grams of short chain triglyceride may increase ketones over 1 mM (e.g., while 5 grams of BHB alone elevate blood ketone levels to only 0.5 mM)

In some implementations, the dihydroberberine may be complexed or otherwise coupled to one or more of the additional compounds in the composition. For example, the composition may include a dihydroberberine-betahydroxybutyrate complex and/or a dihydroberberine-amino acid complex.

EXAMPLE

Example 1

Five subjects were subject to three separate glucose challenge tests (75 g glucose) after administration of 500 mg berberine (BB), 250 mg of dihydroberberine (DHBB) or 500 dihydroberberine. Blood was drawn prior to administration and after 30, 60, 90, 120, and 180 minutes. FIG. 1 illustrates the results of the administration protocol. FIG. 1 illustrates the average blood glucose level of the 5 subjects at each of the times.

As illustrated, unexpectedly, administration of the dihydroberberine resulted in less fluctuations in blood glucose level than berberine. In addition, an unexpected result of the administration of dihydroberberine is that administration of dihydroberberine may keep blood glucose levels closer to fasting blood glucose than berberine.

Example 2

As in Example 1, five subjects were subject to three separate glucose challenge tests (75 g glucose) after administration of 500 mg berberine (BB), 250 mg of dihydroberberine (DHBB) or 500 dihydroberberine. FIG. 2 illustrates a ranking which compositions caused the lowest blood glucose levels during a oral glucose challenge. Unexpectedly, 250 mg of DHBB may control blood glucose levels better than even 500 mg of DHBB. For example, in some individuals (e.g., individuals with moderate glucose tolerance) may achieve better blood glucose control when administered a lower dosage of DHBB. As illustrated, dihydroberberine administration resulted in lower blood glucose than administration of berberine in most individuals.

Example 3

Figure 3:
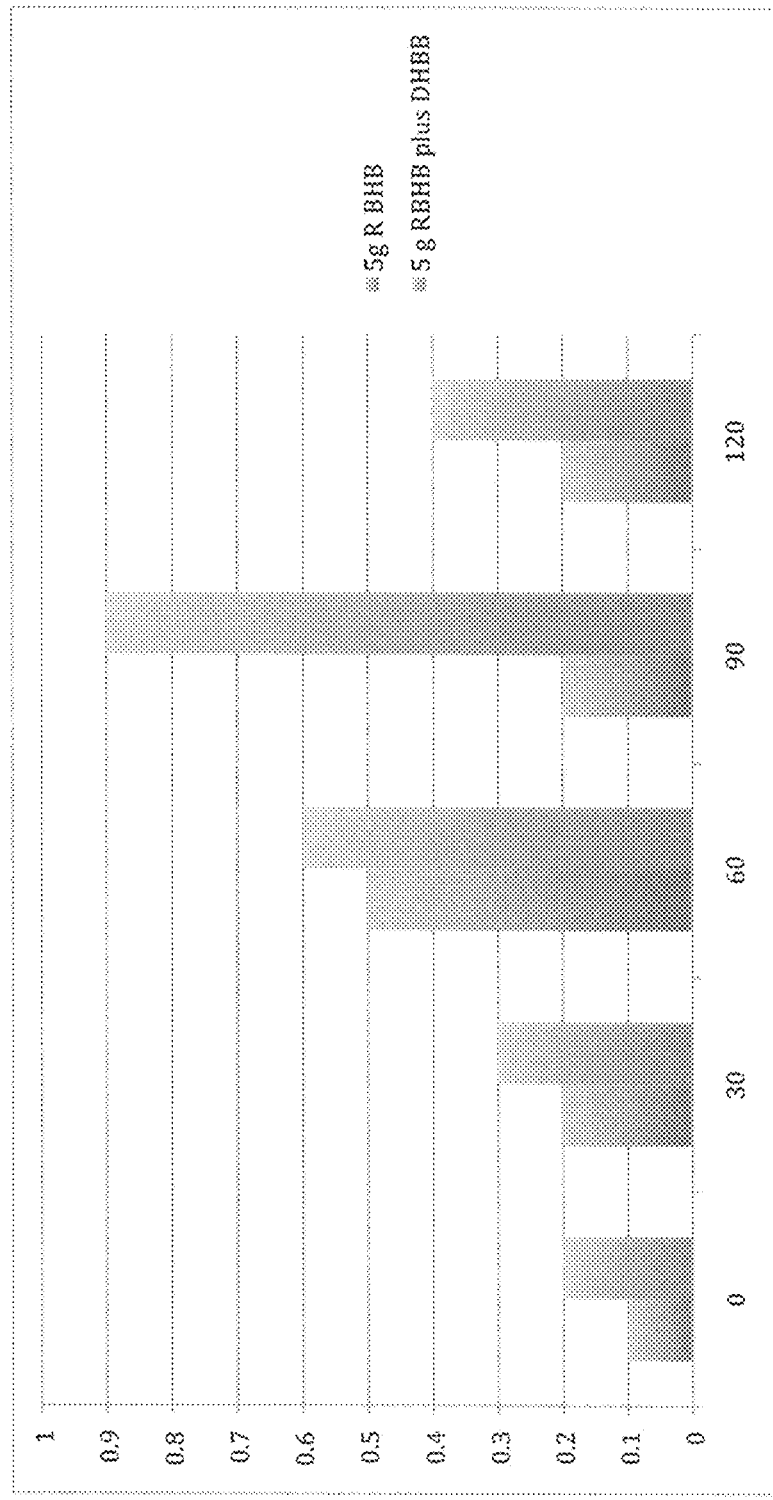
FIG. 3 illustrates a table with blood ketone levels for subjects after administration of an example administration protocol.

A subject was subject to a glucose challenge test (75 g glucose) after administration of 250 mg dihydroberberine (DHBB) and a glucose challenge test after administration of 250 mg dihydroberberine (DHBB) along with 5 mg of beta-hydroxybutyrate (e.g., 5 mg sodium beta-hydroxybutyrate). As illustrated in FIG. 3, blood ketone levels are unexpectedly increased even 120 minutes after the glucose challenge with the administration of an effective amount of dihydroberberine.

Example 4

Five subjects were subject to three separate glucose challenge tests (75 g glucose) approximately 25 minutes after administration of 500 mg berberine (BB), 250 mg of dihydroberberine (DHBB) or 500 dihydroberberine. Blood was drawn prior to administration and after 30, 60, 90, 120, and 180 minutes and tested for glucose levels. FIG. 4 illustrates the results of the administration protocol.

As illustrated, administration of dihyroberberine in individuals with moderate baseline glucose levels moderates blood glucose levels better than even double the quantity of berberine.

End of Example

The described compositions may be administered via any appropriate administration method. For example, the described compositions may be administered enterally and/or parenterally. In some implementations, the described composition may be administered via a tablet and/or capsule. In some implementations, the described composition may be administered via tablet, capsule, powdered supplement; ready-to-drink formulation; topical product including transdermals; cosmeceutical product; foods such bars, cookies, gum, candy, functional foods; toothpaste, sublingual product; injection; intravenous fluids; beverages such as shots or energy shots; inhalers; sublinguals; and/or combinations thereof. The described composition may be provided in a powdered form that allows the described composition to be sprinkled on food, mixed with a liquid to provide a beverage, directly administered.

The described compositions may be administered on an administration protocol to improve glucose tolerance (e.g., fasting glucose levels may be reduced and/or glucose metabolism may be improved), in some implementations. The described compositions may be administered on an administration protocol to increase ketone levels (e.g., blood and/or urine ketone concentrations). For example, the described compositions may be administered once a day, via a time released or extended release preparation, and/or multiple times a day. The described composition may replace other pharmaceuticals taken for improving glucose tolerance, such as metformin, and/or be utilized in combination with one or more other pharmaceuticals, as appropriate.

In some implementations, an administration schedule may include administration of different berberine metabolite compositions at different periods. For example, berberine metabolite compositions may include at least a first composition and a second composition. The first composition may include dihydroberberine. The second composition may include dihydroberberine and a first additional compound that is capable of independently increasing blood ketone levels. The first composition may be administered to an individual for a first period of time and the second composition may be administered to the same individual for a second period of time. In some implementations, a third composition comprising dihydroberberine and a second additional compound that is different from the first additional compound may be administered. The first and other compositions (e.g., second and/or third composition) may be administered alternatively, sequentially, and/or in conjunction with each other (e.g., with a second and/or third composition). The compound formulations (e.g., dihydroberberine and/or which additional compounds are included) may be selected based on user preference (e.g., taste, diseases, sensitivities), desired results (e.g., fast induction of ketosis and/or maintenance), etc.

In various implementations, although a berberine metabolite such as dihydroberberine and/or tetrahydroberberine may be described, other forms of dihydroberberine and/or tetrahydroberberine may be administered such as salts, complexes, and/or derivatives thereof Although various described systems and processes have been described as a being administered in humans, the described systems and processes may be administered to other mammals, such as rats, dogs, etc.

It is to be understood the implementations are not limited to particular systems or processes described which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "a beta-hydroxybutyrate" includes a combination of two or more beta-hydroxybutyrates and reference to "an additive" includes different types and/or combinations of additives.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A method of managing glucose tolerance in an individual, the method comprising:
   administering, to an individual, a pharmaceutically effective amount of dihydroberberine, wherein the pharmaceutically effective amount of dihydroberberine comprises approximately 25 mg to approximately 800 mg of dihydroberberine.

2. The method of claim 1 wherein the administration of dihydroberberine reduces fasting glucose levels.

3. The method of claim 1 wherein the dihydroberberine is administered as a complexed composition, and wherein the complexed composition further comprises at least one of complexed phytosomes or liposomes.

4. The method of claim 1 wherein the dihydroberberine is a microemulsion including dihydroberberine.

5. The method of claim 1 wherein the dihydroberberine is orally administered as a capsule or tablet.

6. The method of claim 1 wherein the dihydroberberine is orally administered as at least one of a food product or beverage product.

7. The method of claim 1 wherein the dihydroberberine is administered at least once daily.

8. The method of claim 1 further comprising administrating a Cytochrome P450 inhibitor, wherein administration of the Cyctochrome P450 inhibitor allows decreasing of the amount of dihydroberberine administered to be sufficient to achieve the desired results.

9. A method of increasing blood ketone levels in an individual, the method comprising:
   administering, to an individual, a pharmaceutically effective amount of dihydroberberine, wherein the pharmaceutically effective amount of dihydroberberine comprises approximately 25 mg to approximately 800 mg of dihydroberberine.

10. The method of claim 9 wherein the dihydroberberine is administered approximately concurrently with meals.

11. The method of claim 9 further comprising administrating, to the individual, a pharmaceutically effective amount of one or more additional compounds capable of independently increasing blood ketone levels.

12. The method of claim 11 wherein the dihydroberberine and at least one of the additional compounds are administered approximately concurrently.

13. The method of claim 11 wherein the dihydroberberine and one or more of the additional compounds are administered at least one time daily.

14. The method of claim 9 wherein the pharmaceutically effective amount of dihydroberberine is administered with one or more additional compounds, and wherein one or more of the additional compounds comprises at least one of a beta-hydroxybutyrate, butyrate, a fatty acid, or ester of fatty acid, and wherein the amount of dihydroberberine administered to be pharmaceutically effective is less than the amount of dihydroberberine administered to be pharmaceutically effective when the dihydroberberine is administered without at least one of the additional compounds.

15. The method of claim 14 wherein at least one of the additional compounds comprises a R-beta-hydroxybutyrate compound.

16. The method of claim 14 wherein one or more of the additional compounds comprises at least one of a beta-hydroxybutyrate salt or beta-hydroxybutyrate polymer.

17. The method of claim 14 wherein the dihydroberberine and at least one of the additional compounds are administered approximately concurrently.

18. The method of claim 14 wherein the composition comprises at least two of the additional compounds, and wherein two or more of the additional compounds comprises a beta-hydroxybutyrate and at least one of a fatty acid or ester of a fatty acid.

19. The method of claim 1 wherein the pharmaceutically effective amount of dihydroberberine is administered with one or more additional compounds, and wherein one or more of the additional compounds comprises at least one of a beta-hydroxybutyrate, butyrate, a fatty acid, or ester of fatty acid.

20. The method of claim 9 wherein the pharmaceutically effective amount of dihydroberberine is administered with a beta-hydroxybutyrate and a medium chain fatty acid.

* * * * *